United States Patent [19]

Tanaka

[11] Patent Number: 4,659,697

[45] Date of Patent: Apr. 21, 1987

[54] ANTIANAEMIC COMPOSITION AND A PROCESS FOR PRODUCING THE SAME

[76] Inventor: Kentaro Tanaka, 1-26, Misaki 1-chome, Kofu-shi, Yamanashi-ken, Japan

[21] Appl. No.: 698,218

[22] Filed: Feb. 4, 1985

Related U.S. Application Data

[60] Division of Ser. No. 496,744, May 20, 1983, abandoned, which is a continuation-in-part of Ser. No. 334,615, Dec. 28, 1981, abandoned.

[51] Int. Cl.$^4$ ............................................. A61K 31/70
[52] U.S. Cl. ..................................... 514/23; 514/502; 514/814; 536/1.1; 536/123
[58] Field of Search ............... 536/17.1, 121, 113; 435/74; 514/502, 814, 23

[56] References Cited

U.S. PATENT DOCUMENTS

| | | | |
|---|---|---|---|
| 1,720,329 | 7/1929 | Heuser | 426/15 |
| 2,820,740 | 1/1958 | London et al. | 536/113 |
| 2,885,393 | 5/1959 | Herb | 536/113 |
| 3,022,221 | 2/1962 | Floramo | 536/113 |
| 3,252,863 | 5/1966 | Lindvall et al. | 536/113 |
| 4,400,199 | 8/1983 | Yokoyama et al. | 71/88 |
| 4,438,093 | 3/1984 | Shimada et al. | 424/50 |

FOREIGN PATENT DOCUMENTS

| | | | |
|---|---|---|---|
| 0014340 | 8/1980 | European Pat. Off. | 426/14 |
| 2339206 | 3/1975 | Fed. Rep. of Germany | 426/15 |
| WO82/02723 | 8/1982 | PCT Int'l Appl. | 426/15 |

OTHER PUBLICATIONS

Reprint from Bulletin of Research Inst. of Fermentation, No. 12 (1966), Yamanashi University.
"The Iron Content of Grapes & Wine:–Ind. & Engin. Chem. 3/15/37, J. Byrne, G. Saywell & W. Cruess, vol. 9.
"The Technology of Wine Making", M. A. Amerine, H. W. Berg, W. V. Cruess 1972.

*Primary Examiner*—Johnnie R. Brown
*Attorney, Agent, or Firm*—Sprung Horn Kramer & Woods

[57] ABSTRACT

A process for producing an organoiron(II) compound-containing antianaemic composition which comprises cultivating a yeast in a saccharide-containing nutrient medium therefor in the presence of an iron compound to form a cultured broth comprising an organoiron(II) compound, alcohol and water and removing the alcohol from the cultured broth to an extent that the resulting cultured broth has an alcohol content of less than about 1% by volume, and an antianaemic composition produced thereby. The antianaemic composition of the present invention is very stable, and excellent in absorbability into a living body and incorporation of iron into hemoglobin.

8 Claims, 1 Drawing Figure

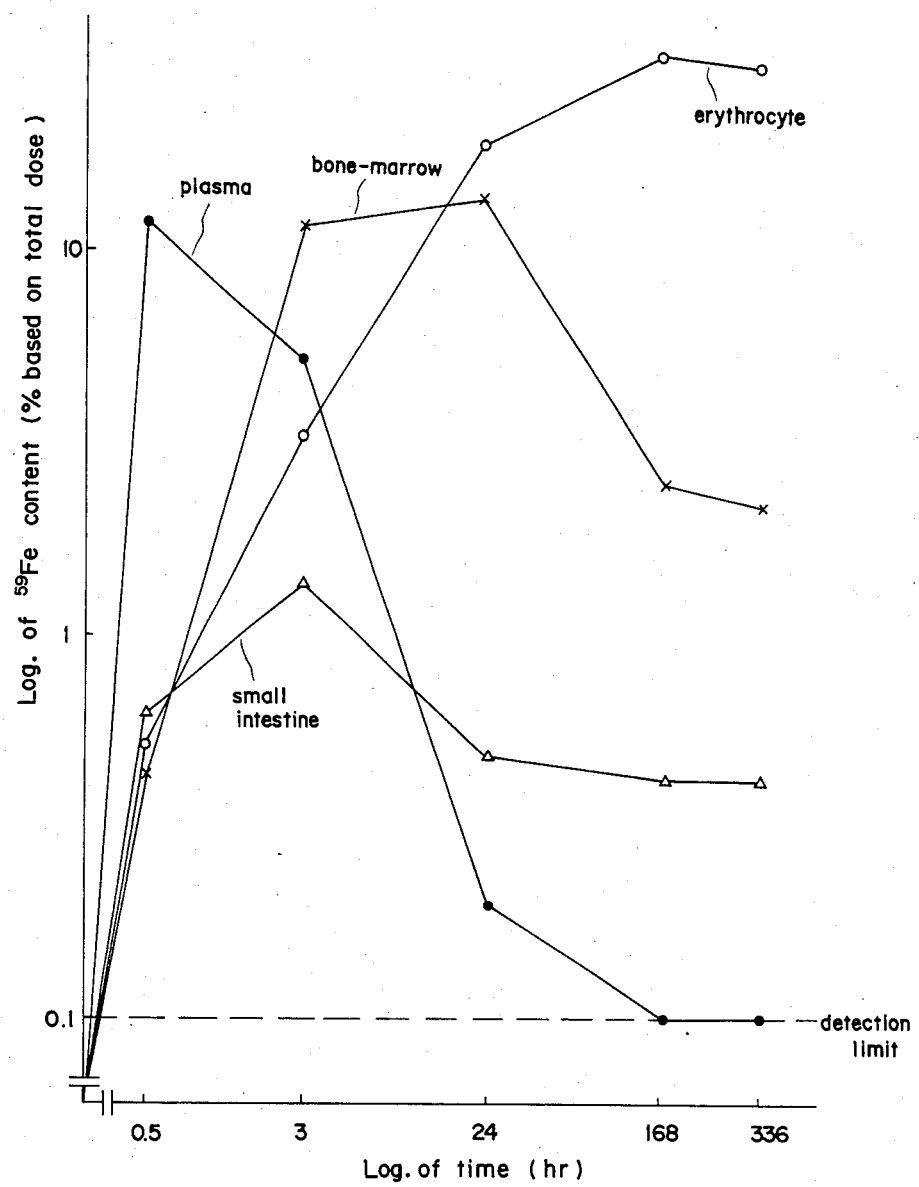

ANTIANAEMIC COMPOSITION AND A PROCESS FOR PRODUCING THE SAME

This is a division of application Ser. N. 496,744, filed May 20, 1983, now abandoned, which is a continuation-in-part of application Ser. No. 334,615, filed Dec. 28, 1981, now abandoned.

This invention relates to an antianaemic composition and a process for producing the same. More particularly, the present invention is concerned with an organoiron(II) compound-containing antianaemic composition which can be well absorbed into the living body and is chemically stable and the production of the same by a process comprising cultivating a yeast in a saccharide-containing nutrient medium in the presence of an iron compound, followed by removal of alcohol.

Since iron is a major constituent of hemoglobin, various kinds of iron compounds are used as an antianaemics. Heretofore, a considerable number of researches have been made on the absorption of iron into a living body through the stomach and intestine organs. As a result, it is now known that $Fe^{++}$ can be well absorbed in the human organs but $Fe^{+++}$ is not. Accordingly, divalent iron compounds such as ferrous sulfate are most frequently used as a chalybeate. When using divalent iron compounds as a chalybeate, however, special pharmaceutical techniques such as coating should be applied because they are readily oxidized to trivalent iron compounds. It is also known that an iron complex with an brganic acid, chelating agent, sugar, amino acid or the like is better absorbed into a living body than inorganic iron compounds. Practically, an organic acid salt of a divalent iron such as ferrous fumarate or ferrous succinate, or a divalent iron chelate has been used for the remedy of a patient suffering from anaemia. Such ferrous compounds, however, still have a disadvantage that they tend to easily be oxidized to the corresponding ferric compounds during the storage or in the living body even after administration thereof to a patient.

On the other hand, wine has long been believed to be effective for the remedy of a patient suffering from anaemia, but any elucidation has not yet been made as to whether the iron values contained in wine are really effective as a chalybeate, or as to in what state the iron values in wine exert an antianaemic effect even if they are admitted to be effective. Further, there is not any accepted conviction as to where the iron values contained in wine originate. Furthermore, the iron content in the wine put on the market widely varies. Therefore, drinking wine does not always ensure absorption of iron into the living body.

The present inventor has made extensive and intensive researches on the iron values contained in wine. Illustratively stated, the present inventor has conducted the analysis of an iron content of the raw material (grape juice) for wine and found that an amount of iron to which the iron content present in the wine put on the market can be attributed is not contained in the ordinary raw material for wine and that most of the iron values present in the wine put on the market is due to contamination during the fermentation stage. Further, the present inventor has studied the state of iron values present in wine, which is effective for the use as a chalybeate. Based on the findings, study and the subsequent studies for developing an antianaemic agent, the present invention has been made.

Accordingly, it is an object of the present invention to provide a process for producing an organoiron(II) compound-containing antianaemic composition which can be efficiently absorbed into a living body and chemically stable.

It is another object of the present invention to provide a process of the above-mentioned kind which can be carried out easily at low cost.

It is a further object of the present invention to provide an organoiron(II) compound-containing antianaemic composition produced by a process as mentioned above.

The foregoing and other objects, features and advantages of the present invention will be apparent to those skilled in the art from the following detailed description taken in connection with the accompanying drawing in which:

FIGURE shows graphs of the relationships between the iron contents in the living body at its plasma, bone-marrow, erythrocyte and small intestine and the lapse of time after administration of the present antianaemic composition.

In one aspect of the present invention, there is provided a process for producing an organoiron(II) compound-containing antianaemic composition which comprises: (1) cultivating a yeast in a saccharide-containing nutrient medium in the presence of an iron compound to form a cultured broth comprising an organoiron(II) compound, alcohol and water, and (2) removing the alcohol from the cultured broth to an extent that the resulting cultured broth has an alcohol content of less than about 1% by volume. The kind of a yeast is not critical, but a wide variety of general ordinarily employed in fermentation may be employed. Preferable genus is Saccharomyces or Metschnikowia. Examples of species of yeast which may preferably be employed are shown in Table 1.

TABLE 1

| | Species | Strain |
|---|---|---|
| 1. | Saccharomyces cerevisiae | OC-2 |
| 2. | Metschnikowia pulcherrima | K-427 |
| 3. | Saccharomyces chevalieri | IAM-4861 |
| 4. | Saccharomyces bayanus | PW-15 |
| 5. | Saccharomyces italicus | PW-27 |
| 6. | Saccharomyces fermentati | WF-107 |
| 7. | Saccharomyces rosei | 28-t |
| 8. | Saccharomyces heterogenicus | PW-25 |

Note: The species and strains listed in Table 1 are all known. Of the above-mentioned species, Saccharomyces cerevisiae is most preferred because it can produce a large quantity of a fraction B having an excellent absorbability through the intestine as will be explained later.

Examples of the saccharide-containing nutrient medium to be employed in the present invention include fruit juice, semi-synthetic culture medium and synthetic culture medium. Specific examples of the fruit juice include grape juice (or must), apple juice and the like. Of substances of saccharide, saccharose such as sucrose, glucose, fructose or the like may more preferably be employed. Preferred examples of semi-synthetic medium and synthetic nutrient medium are given in Tables 2 and 3, respectively.

TABLE 2

| (semi-synthetic) | |
|---|---|
| D-glucose | 100.0 g |
| $(NH_4)_2SO_4$ | 5.0 g |
| $KH_2PO_4$ | 1.0 g |
| $MgSO_4.7H_2O$ | 0.50 g |
| NaCl | 0.10 g |

TABLE 2-continued

| (semi-synthetic) | |
| --- | --- |
| $CaCl_2.2H_2O$ | 0.10 g |
| Yeast extract | 1.0 g |
| Distilled water | 1000 ml |
| Initial pH | 6.0 |

TABLE 3

| (synthetic) | |
| --- | --- |
| D-glucose | 150 g |
| $(NH_4)_2SO_4$ | 3.5 g |
| $KH_2PO_4$ | 1.0 g |
| $MgSO_4.7H_2O$ | 0.50 g |
| NaCl | 0.10 g |
| $CaCl_2.2H_2O$ | 0.1 g |
| $H_3PO_3$ | 500 μg |
| $CuSO_4.5H_2O$ | 40 μg |
| KI | 100 μg |
| $FeCl_3.6H_2O$ | 242 mg |
| $MnSO_4.H_2O$ | 400 μg |
| $Na_2MoO_4.2H_2O$ | 200 μg |
| Biotin | 2 μg |
| $ZnSO_4.7H_2O$ | 400 μg |
| Calcium pantothenate | 400 μg |
| Inositol | 2000 μg |
| Thiamine.HCl | 400 μg |
| Distilled water | 1000 ml |
| Initial pH | 7.0 |

The kind of artificial nutrient medium, of course, is not limited to the above-mentioned examples, and any formulations employable in an ordinary fermentation using saccharide-containing nutrient medium may be employed. As the iron compound, any of those which can be ionized with respect to iron may be employed. As specific examples, there can be mentioned inorganic acid salts of iron such as ferric chloride, ferrous sulfate and ferric sulfate and organic acid salts of iron such as iron citrate and iron tartrate. Iron powder is also useful, but disadvantageously needs a long period of time for its dissolution into a culture medium. From the viewpoints of solubility, availability and non-toxicity, the above-mentioned iron compounds are preferred. Such an iron compound, when it is of trivalent iron, is converted to produce ferrous ions during the fermentation. The amount of the iron compound to be added is not critical, but even if the amount of iron added is increased, the amount of iron in the product is not necessarily increased in proportional relationship. Further, the addition of too large an amount of the iron compound adversely suppresses the progress of fermentation. On the other hand, the use of too small an amount of the iron compound cannot exert the intended effect. Usually, the iron compound may be employed in the nutrient medium at a concentration of about 10 to about 70 ppm, more preferably about 30 to about 50 ppm in terms of amount of iron.

In practicing the present invention, whether the fruit juice, semi-synthetic culture medium or synthetic medium is used, the yeast may be employed at a yeast population of about $5 \times 10^5$ to about $3 \times 10^6$/ml of culture medium.

Further fermentation conditions are given as follows. (1) In the case of a culture medium of fruit juice, the cultivation of a yeast can be carried out according to a customary process for the production of wine. For example, the fruit juice, e.g., grape juice or apple juice, as such, or after a saccharide such as glucose, fructose, sucrose or the like is added thereto in such an amount as will exhibit a refraction saccharide degree of about 20 to about 25, is subjected to treatment with a small amount of a germicide (e.g., about 100 ppm of potassium metabisulfite) to kill contaminating microorganisms such as wild yeast. Then, the cultivation may usually be conducted at room temperature to 30° C. under atmospheric pressure for about 15 days. (2) In the case of a semi-synthetic culture medium or a synthetic culture medium, the cultivation may be conducted at about 18 to about 30° C. under stationary condition or anaerobic condition. The amount of a saccharide in the nutrient medium is not critical. From a viewpoint of provision of better conditions of the desired fermentation, the saccharide may generally be incorporated into the nutrient medium in an amount of about 5 to about 25% by weight, more preferably about 10 to about 15% by weight based on the nutrient medium.

The pH of the artificial nutrient medium has initially a value of about 6 to about 7. However, 3 to 4 hours after the initiation of fermentation, the pH value rapidly decreases to 3.6 to 3.8 (This value does not change thereafter) and then the rate of fermentation remarkably increases. Fermentation is continued for a period of from about 10 to about 20 days.

The resulting cultured broth, which contains an organoiron(II) compound, alcohol and water, is subjected to removal of alcohol at a temperature not exceeding 30° C. under a pressure of about 15 to 20 mmHg to such an extent that the alcohol concentration of the cultured broth is decreased to less than 1% by volume. The removal of alcohol from the cultured broth may be efficiently effected by any of the commonly-known techniques, for example, using a rotary evaporator.

The alcohol concentration of the cultured broth may be traced by determining the specific gravity of each aliquot taken out from the cultured broth. Illustratively stated, an aliquot is taken out from the cultured broth, and the specific gravity of the aliquot at a predetermined temperature is measured. Then, the alcohol concentration corresponding to the specific gravity is read on the graph obtained by plotting the specific gravity of each solution having a known alcohol concentration against the alcohol concentration.

The method for determining the alcohol concentration is not limited to the above-explained method, but in fact any other appropriate method, including chromatography, can be employed.

As mentioned above, the cultured broth is subjected to removal of alcohol to such an extent that the alcohol concentration of the cultured broth is decreased to less than 1% by volume. The reason is that if the cultured broth having a high alcohol concentration of 1% by volume or more is continually administered as an antianaemic composition to a patient for a prolonged period of time, it adversely affects the health of the patient.

The antianaemic composition produced by the present process can, first, be obtained in the form of a cultured broth. The cultured broth may then be separated into a precipitate and a supernatant, for example, by centrifugation or the like. The supernatant is also one form of the present antianaemic composition. In any of them, there is contained a water-soluble organoiron(II) compound which is believed to be an organic complex of divalent iron and is a fermentation product of iron formed by the initially added iron compound's undergoing a chemical reaction during the cultivation or fermentation. Both the cultured broth and the supernatent as such can be administered. For example, when the culture medium is grape juice, they can be enjoyed by people as an organoiron(II)-containing elixir. The concentrates may be ultimately concentrated to dryness, and the resultant as such or, if desired, together with a reducing additive such as Vitamin C, may be formulated into the adequate form for oral administration, for example, a tablet, capsule, powder, granule or fine granule form. If desired, these dosage forms may be easily prepared according to conventional technique and may comprise commonly employed excipients, binding agents, disintegrators, glidants and other pharmaceutical agents. As the excipient, binding agent and/or disintegrator, there may be, for example, mentioned microcrystalline cellulose, wheat starch, sugar, lactose, gum arabic, tragacanth gum, carboxymethylcellulose and so on. As the glidant, there may be given, e.g., magnesium stearate and talc. Tablets may be also coated according to conventional coating procedures and any commonly employable coating materials such as, for example, shellac, ethylcellulose, hydroxymethylcellulose, polyvinyl pyrrolidone, titanium dioxide and the like may be favorably applied for such purposes. The dosage may vary depending upon ages, severities and body weights of patients, but the present antianaemic composition may be usually administered in a daily dose of from about 5 mg to about 100 mg in terms of amount of iron for adults, if necessary, in divided dosage forms.

Thus, in another aspect of the present invention, there is provided an organoiron(II) compound-containing antianaemic composition produced by a process comprising:

(1) cultivating a yeast in a saccharide-containing nutrient medium in the presence of an iron compound to form a cultured broth comprising water, alcohol and an organoiron(II) compound, and (2) removing the alcohol from the cultured broth to an extent that the resulting cultured broth has an alcohol content of less than about 1% by volume.

As stated before, from the chemical analysis, it is believed that the active ingredient of the present antianaemic composition is a divalent iron-containing organic complex composed only of elements Fe, C, H and O whose molecular weight is in the range of about $10^2$ to about $5 \times 10^3$. As is apparent from Experiment which will be given later, it is clearly recognized that the organoiron(II) in the present antianaemic composition is much more effective in capability of being absorbed in the living body of a human being and animals and incorporation into hemoglobin than the conventional chalybeates. Furthermore, it is clearly recognized that the organoiron(II) in the present antianaemic composition is remarkably stable as compared with divalent iron compounds such as ferrous chloride, ferrous sulfate, ferrous fumarate, ferrous succinate and ferrous tartrate.

When the supernatant as mentioned before is subjected to chromatographic fractionation, for example, by means of Amberlite XAD-2(available from Rohm and Haas Co., U.S.A), it is separated into two fractions, namely, Fraction A and Fraction B. In this connection, Fraction B has a relatively low molecular weight but a high absorbability into the living body as compared with Fraction A.

In still another aspect of the present invention, there is provided a method of increasing an iron content in blood which comprises administering to a patient an effective amount of an organoiron(II) compound-containing antianaemic composition produced by a process comprising:

(1) cultivating a yeast in a saccharide-containing nutrient medium in the presence of an iron compound to form a cultured broth comprising an organoiron(II) compound, alcohol and water, and (2) removing the alcohol from the cultured broth to an extent that the resulting cultured broth has an alcohol content of less than about 1% by volume.

The present invention will be illustrated in more detail with reference to the following Examples, which should not be construed to be limiting the scope of the present invention.

EXAMPLE 1

Sugar was added to grape juice from Koshu grape (produced in the vicinity of Kofu-city, Japan) in such an amount as would give a refraction saccharide degree of 24. To the mixture was added potassium metabisulfite in an amount of 100 ppm in terms of amount of sulfurous acid. Then, $FeCl_3$ was added in an amount of 50 ppm in terms of amount of iron, and a yeast mash of *Saccharomyces cerevisiae* OC-2 was added in an amount of 3% by volume based on the grape juice. The mixture was subjected to fermentation at 20° C. for 15 days. The resulting fermentation product was subjected to removal of alcohol at 25° C. under a reduced pressure of 15 mmHg, using a rotary evaporator, to an extent that the alcohol concentration of the cultured broth was decreased to 0.5% by volume to obtain an antianaemic composition. The iron content of the composition was 31 ppm.

EXPERIMENTS

Animal tests were conducted to show the effectiveness of the iron values in the wine prepared according to the present invention.

(1) Preparation of Test Sample (a) Wine according to the present invention

Sugar was added to grape juice from Koshu grape in such an amount as would give a refraction saccharide degree of 24.To the mixture was added potassium metabisulfite in an amount of 100 ppm in terms of amount of sulfurous acid. On the other hand, $^{59}FeCl_3$ was added to a solution of ferric chloride in 0.1N hydrochloric acid in such an amount as would give a specific radioactivity of 6.25 $\mu$Ci/50 $\mu$gFe, and the pH of the mixture was adjusted to pH 3by adding an aqueous 0.1N sodium hydroxide solution. This was added to the above-prepared grape juice medium in an amount of 50 ppm in terms of amount of iron. Then, a yeast mash of *Saccharomyces cerevisiae* OC-2 was added in an amount of 3% by volume based on the iron-containing grape juice medium. Fermentation was conducted at about 20° C. After completion of the intended fermentation, the mixture was subjected to centrifugation at 10,000 rpm for 10 minutes to obtain wine containing $^{59}Fe$. Removal of alcohol was performed under reduced pressure at 30° C. to an extent that the alcohol concentration of the wine was decreased to 0.5% by volume, and test samples respectively containing 10, 40, 80 and 250 $\mu$gFe/ml were prepared by addition of distilled water.

(b) Ferrous sulfate solution (Comparative)

Put into the $^{59}FeCl_3$ solution with a specific radioactivity of 12.5 $\mu$Ci/$\mu$gFe was ascorbic acid in an amount of 0.05$\mu$ mol per $\mu$g of iron to give divalent iron. By mixing this with an aqueous ferrous sulfate solution, comparative test samples having 5 µCi/10, 40, 80 and 250 µgFe/ml and a pH value of 3 were obtained.

(c) Ferric chloride solution (Comparative)

Put into the $^{59}FeCl_3$ solution was an aqueous ferric chloride solution, and the pH of the mixture was adjusted to pH 3 by adding an aqueous sodium hydroxide solution. Comparative test samples having 5 µCi/10, 40, 80 and 250 µgFe/ml were obtained.

(d) Concentrated wine-ferrous sulfate mixture (Comparative)

Wine (in which the iron originating in grape juice is present in an amount of about 1 ppm) prepared in the same procedures as described in Example 1 except that $FeCl_3$ was not added was concentrated to ¼ in volume. By mixing this with the ferrous sulfate solution (prepared according to the above-mentioned procedures and having 10 µCi/80 µgFe/ml) at a ratio of 1:1 by volume, a comparative test sample having 5 µCi/40 µgFe/ml was obtained.

(2) Administration

Five-week old male Sprague-Dawly rats (available from Nippon Kurea K.K., Japan) were subjected to preparatory breeding for one week. They were fed with a feed "CA-1" (containing iron in an amount of 31.5 mg/100 g, and manufactured and sold by Nippon Kurea K.K., Japan), and city water was given. During the preparatory breeding, weight increase was checked. Those rats having a body weight of about 160 g at the age of six weeks were subjected to the experiments. Through the period of experiments, the rats were bred in a metabolic cage. No feeding was done for 18 hours before administering a test sample, but distilled water was continued to be given. Each test sample prepared according to the above-mentioned procedures was administered to a group of five rats, directly into their stomach by means of stomach probe, in an amount of 1 ml/160 g body weight. Six hours after administering the test sample, feeding of feed "CA-1" was resumed.

(3) Determining Radioactivity of In-vivo Sample:

After administering each test sample, feces and urine were taken at intervals of hours to determine radioactivities thereof. 50 µl of blood was taken by means of a heparin-treated capillary from the tail vein at intervals of hours, and subjected to centrifugation at 3,000 rpm for 5 minutes to separate blood corpuscles from plasma. Radioactivities of the so obtained blood corpuscles and plasma were determined. Absorption of iron into the body and incorporation of the body-absorbed iron into hemoglobin are shown in Table 4.

TABLE 4

(Comparison between organoiron(II)-containing wine, inorganic ferrous compound and inorganic ferric compound, with respect to absorbability into the living body and incorporation of iron into hemoglobin)

| Iron concentration in sample (µg/ml) | Dose (Fe µg/ kg · body weight) | Kind of sample | A Absorbability (%) | B Incorporation into Hemoglobin (%) | B/A Utility of absorbed iron (%) |
|---|---|---|---|---|---|
| 10 | 62.5 | (a) | 69.4 ± 1.4 | 48.0 ± 1.8 | 69.2 ± 1.5 |
|  |  | (b) | 67.4 ± 3.6 | 47.5 ± 1.8 | 70.5 ± 2.5 |
|  |  | (c) | 50.1 ± 4.2 | 32.0 ± 6.2 | 63.9 ± 2.6 |
| 40 | 250 | (a) | 53.5 ± 1.7 | 28.5 ± 2.3 | 53.3 ± 2.5 |
|  |  | (b) | 37.6 ± 4.0 | 20.0 ± 1.9 | 53.2 ± 4.0 |
|  |  | (c) | 29.9 ± 6.9 | 15.7 ± 4.2 | 52.5 ± 4.5 |
|  |  | (d) | 31.0 ± 3.5 | 17.9 ± 3.2 | 57.7 ± 3.5 |
| 80 | 500 | (a) | 35.5 ± 4.6 | 17.1 ± 2.3 | 48.2 ± 4.5 |
|  |  | (b) | 20.0 ± 4.0 | 10.5 ± 1.9 | 52.5 ± 10.5 |
|  |  | (c) | 16.5 ± 3.1 | 7.2 ± 2.0 | 43.6 ± 3.1 |
| 250 | 1500 | (a) | 23.5 ± 3.5 | 7.2 ± 0.9 | 30.6 ± 3.0 |
|  |  | (b) | 9.7 ± 4.5 | 3.8 ± 2.0 | 39.2 ± 8.0 |
|  |  | (c) | — | — | — |

Note
A (absorbability) = 100 × (1 − amount of discharged $^{59}Fe$/amount of total dose of $^{59}Fe$); and
B (Incorporation into Hemoglobin): $^{59}Fe$ content in the whole blood at the time of 168 hours after administration of sample.
Each figure represents a mean value ± standard error.

As is apparent from Table 4, when the iron concentration in administered sample of the present composition is as low as about 1 mg/liter or less, there is not a remarkable difference in absorbability into a living body between the organic iron complex according to the present invention and the inorganic iron salts. This is assumed to be attributed to the fact that such an iron concentration as low as about 1 mg/liter or less is within such a range that the reducing capacity of the living body itself is sufficient therefor. But, when the iron concentration is relatively high, the antianaemic composition according to the present invention exhibits a remarkably improved absorbability into the living body as compared with $FeSO_4$ and $FeCl_3$. On the other hand, no significant difference in absorbability into the living body is seen between the mixture of concentrated ordinary wine and ferrous sulfate [i.e. (d) in Table 4] and ferrous sulfate per se [i.e. (c) in Table 1].

EXAMPLE 2

Substantially the same procedures as in Example 1 were repeated except that a semi-synthetic culture medium of Table 2 was employed as the nutrient medium. The mixture was subjected to fermentation at 30° C. for 15 days. The cultured broth was subjected to removal of alcohol at 20° C. under a reduced pressure of 10 mmHg to an extent that the alcohol concentration of the cultured broth was decreased to 0.3% by volume to obtain an antianaemic composition. The iron content of the composition was 35 ppm. The organoiron(II) compound-containing composition was very stable and excellent in antianaemic activity.

EXAMPLE 3

Substantially the same procedures as in Example 1 were repeated except that a synthetic culture medium of Table 3 was employed as the nutrient medium. The mixture was subjected to fermentation at 30° C. for 15 days. The cultured broth was subjected to removal of alcohol at 20° C. under a reduced pressure of 10 mmHg to an extent that the alcohol concentration of the cultured broth was decreased to 0.7% by volume, followed by filtration to obtain a supernatant. The iron content of the supernatant was 33 ppm. The organoiron(II) compound-containing supernatant was very stable and excellent in antianaemic activity.

Turning now to FIGURE, there are shown the relationships between the iron contents in the living body at its plasma, bone-marrow, erythrocyte and small intestine and the lapse of time after administration of the sample prepared from the supernatant obtained in Example 2 and containing 250 μg Fe/ml in a total dose of 250 μg Fe/kg·body weight. The tests were carried out in substantially the same manner as in the above-mentioned Experiments, items 2) and 3) to determine the change in iron content in the living body at its plasma, bone-marrow, erythrocyte and small intestine with the lapse of time after the administration. As is clearly seen from FIGURE, first, the iron content in the plasma rapidly increases but, in turn, rapidly decreases to reach nearly zero about 168 hours after the administration. Instead, second, the iron content in the bone-marrow increases and begins to decrease about 20 hours after the administration. Third, the iron content in the erythrocyte gradually increases to reach a plateau region (in which the iron content is larger than those observed with respect to the plasma and the bone-marrow) and the iron content in the erythrocyte which has once reached the plateau region does not change for about 50 days. The graphs suggest that the iron values absorbed in the plasma are transferred to the erythrocyte through the bone-marrow. The graphs also show that the organoiron(II) compound of the present antianaemic composition is very stably absorbed into the living body and that the incorporation of iron into hemoglobin is very large. Therefore, the times of dosage can advantageously be reduced.

What is claimed is:

1. An antianaemic composition produced by a process comprising:
    (1) cultivating a yeast in a population of $5 \times 10^5$ to $3 \times 10^6$/ml of a medium selected from the group consisting of a grape juice, an apple juice, a semi-synthetic culture medium and a synthetic culture medium, said medium containing a saccharose in 5 to 25% by weight, in the presence of 10 to 70 ppm, in terms of iron, of an iron compound to form a cultured broth comprising water, alcohol and an organoiron (II) compound which is a divalent iron-containing complex composed of Fe, C. H. and O and having a molecular weight in the range of about $10^2$ to about $5 \times 10^3$, and
    (2) removing the alcohol from the cultured broth to an extent that the resulting cultured broth has an alcohol content of less than about 1% by volume.

2. A method of increasing an iron content in blood which comprises administering to a patient an effective amount of an antianaemic composition produced by a process comprising:
    (1) cultivating a yeast in a population of $5 \times 10^5$ to $3 \times 10^6$/ml of a medium selected from the group consisting of a grape juice, an apple juice, a semi-synthetic culture medium and a synthetic culture medium, said medium containing a saccharose in 5 to 25% by weight, in the present of 10 to 70 ppm, in terms of iron, of an iron compound to form a cultured broth comprising water, alcohol and an organoiron (II) compound which is a divalent iron-containing complex composed of Fe, C. H. and O and having a molecular weight in the range of about $10^2$ to about $5 \times 10^3$, and
    (2) removing the alcohol from the cultured broth to an extent that the resulting cultured broth has an alcohol content of less than about 1% by volume.

3. A composition according to claim 1, wherein the iron compound is incorporated into the nutrient medium in an amount of 30 to 50 ppm in terms of amount of iron.

4. A composition according to claim 1, wherein the yeast is of the genus Saccharomyces or Metschnikowia.

5. A composition according to claim 4, wherein the yeast is Saccharomyces cerevisiae, Metschnikowia pulcherrima, Saccharomyces chevalieri, Saccharomyces bayanus, Saccharomyces italicus, Saccharomyces fermentati, Saccharomyces rosei or Saccharomyces heterogenicus.

6. A composition according to claim 1, wherein the iron compound is ferric chloride, ferrous sulfate, ferric sulfate, iron citrate or iron tartrate.

7. A composition according to claim 1, wherein the nutrient medium is a semi-synthetic culture medium or a synthetic culture medium.

8. A composition according to claim 1, which further comprises subjecting a resulting cultured broth to separation to isolate a supernatant.

* * * * *